United States Patent [19]
Uehara et al.

[11] 3,973,186
[45] Aug. 3, 1976

[54] GAS ANALYZING METHOD AND APPARATUS FOR PERFORMNG THE SAME

[75] Inventors: Hiromichi Uehara; Mitsutoshi Tanimoto, both of Sagamihara; Yasuharu Ijuin, Kodaira, all of Japan

[73] Assignee: Sagami Chemical Research Center, Tokyo, Japan

[22] Filed: Aug. 28, 1974

[21] Appl. No.: 501,231

[30] Foreign Application Priority Data
Sept. 5, 1973    Japan.................................. 48-99195

[52] U.S. Cl. ........................ 324/58.5 A; 23/254 E; 324/.5 R; 324/58.5 C; 324/.5 AC
[51] Int. Cl.².......................................... G01R 27/04
[58] Field of Search................. 324/58.5 R, 58.5 A, 324/58.5 B, 58.5 C, 0.5 AH, 0.5 A, 0.5 B, 0.5 AC; 23/254 E, 255 E

[56] References Cited
UNITED STATES PATENTS
2,849,613    8/1958    Dicke............................. 324/58.5 C
3,691,454    9/1972    Hrubesh et al................. 324/58.5 C OTHER PUBLICATIONS
"Molecular Dipole Moments and Stark Effect" by Townes et al., Physical Review, vol. 77, No. 4, Feb., 1950, pp. 500–505, QC–1; P–4.

"Plane Parallel Plate Transmission Line Stark Microwave Spectrograph" by S. A. Marshall, Review of Scientific Instruments, vol. 28, No. 2 Feb., 1957 pp. 134–137.

*Primary Examiner*—Saxfield Chatmon, Jr.
*Attorney, Agent, or Firm*—Oblon, Fisher, Spivak, McClelland & Maier

[57]    ABSTRACT

A gas sample including polar molecules is introduced into a cavity (an internal space) of a cavity resonator, the cavity being provided therein with a Stark electrode which is vertically of a microwave electric field resonating at the microwave frequency, and a direct current Stark voltage which is applied to the Stark electrode together with a sine wave modulation voltage is swept, resulting in a microwave absorption spectrum representing the polar molecules in the gas sample. The resonance frequency of the cavity may be made variable to observe various polar molecules individually.

5 Claims, 9 Drawing Figures

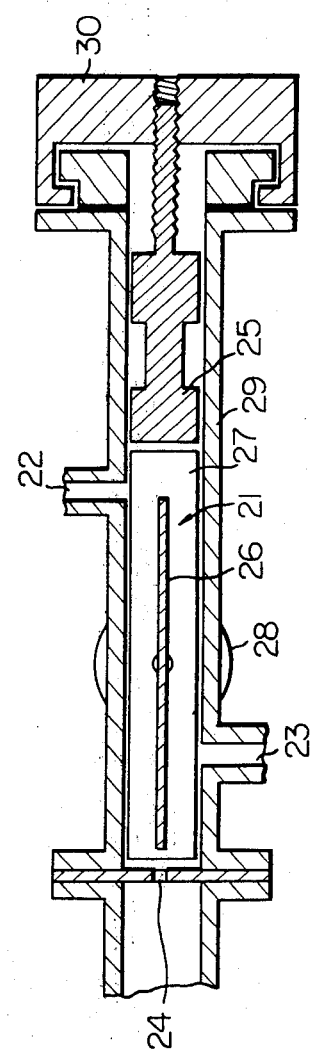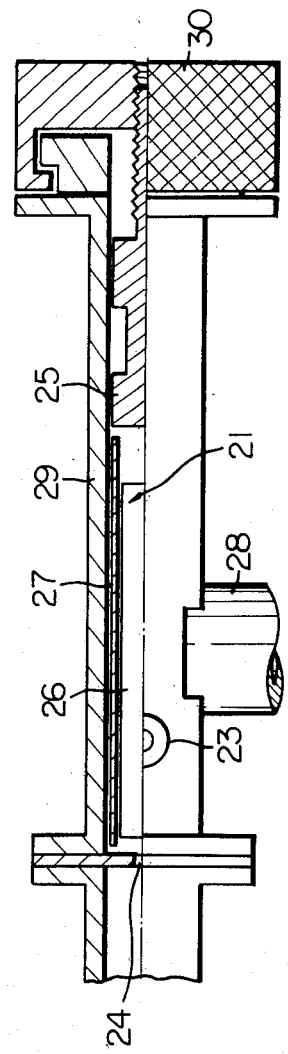
Fig. 2
Fig. 3

GAS ANALYZING METHOD AND APPARATUS FOR PERFORMNG THE SAME

BACKGROUND OF THE INVENTION

The present invention relates to an analysis of gaseous polar molecules, and, in particular, to a simple and high sensitive measuring method of injurious gas components for human health and to an apparatus for performing the same method.

It is well known that the polluted city air, factory exhaust smokes and/or the automobile exhaust gases include injurious substances for human health and the demand of detecting and measuring these substances with high sensitivity has been increased recently. For this purpose, the gas chromatography or the mass spectrometer has been utilized heretofore. In either of the conventional apparatus, however, considerably complicated operations are required to identify these substances contained by a very small amount in the sample gas having a very complex composition and to measure the amount thereof.

It has been known that most of the air polluting substances are polar molecules having dipole moments and have different energy absorption bands in the microwave region which are inherent to the respective molecules. One of the important features of the absorption in the microwave region is that it produces well resolved spectrum. Therefore, it is easy to identify and measure some very small amount of substance exactly from the position of absorption, i.e., absorption spectrum irrespective of the composition of the sample gas including the substance.

In the conventional gas analyser utilizing the microwave absorption, a waveguide cell or Fabry-Pérot type resonator is used and the detection of spectrum is performed by sweeping microwave frequency. In the case of the waveguide cell, the length thereof must be at least several meters in order to obtain a sufficiently high detection sensitivity. However, since it is not practical to produce and to use such long cell, the sensitivity could not be obtained accordingly. The Fabry-Pérot type resonator is essentially larger in size than the cavity resonator. In the latter case complicated apparatus and/or complicated regulations of the apparatus are usually required to provide an appropriate frequency sweeping.

SUMMARY OF THE INVENTION

An object of the present invention is to provide a gas analysis method capable of almost completely removing the defects inherent to the aforesaid conventional methods. Another object of the present invention is to provide an apparatus for performing the same method.

These objects of the present invention are achieved by an employment of a specially designed cavity resonator as a sample cell. In the previously mentioned conventional techniques, the absorption spectrum is detected by sweeping the microwave frequency. In the present invention, the spectrum of an intended molecule is detected by changing a direct current voltage magnitude applied to a Stark electrode plate equipped within a cavity resonator (sample cell) to which a microwave energy of a constant frequency is applied to make it to resonate at the frequency.

It is well known that the energy level of a certain polar molecule in an electric field is shifted due to the Stark effect. Therefore, when a microwave energy is irradiated to the molecule to which the electric field is applied, the molecule will absorb a microwave energy of a frequency different from that when no electric field is applied. Accordingly, when the microwave frequency is fixed at the resonance frequency of the cavity resonator and when an electric field is applied thereto to shift the energy level of the molecule and varied until an interval between the shifted levels becomes equal to the energy corresponding to the fixed microwave frequency of the cavity resonator, an absorption will be observed. That is, instead of the frequency sweeping as in the conventional microwave gas analyser, the detection, the identification and the quantitative measurement of gaseous molecules can be performed by sweeping the Stark voltage.

DESCRIPTION OF THE DRAWINGS

FIG. 2 is a detailed cross-sectional side view of a cavity resonator used in the gas analyser in FIG. 1;

FIG. 3 is a detailed, partially cross-sectioned plane view of the cavity resonator in FIG. 2.

DESCRIPTION OF EMBODIMENTS

One example of the cavity resonator is that of $TE_{10n}$ mode having a rectangular cross section, as will be described hereinafter, and is provided with a sample inlet port for introducing the sample gas into the interior of the cavity thereof and a gas exit port. The microwave energy is introduced into the cavity through a coupling hole. The Stark electrode is a metal plate and it is disposed along the center line of the shorter side of the rectangular and vertically of the microwave electric field within the cavity, with the microwave coupling hole provided at the center of a cavity end plate. With this arrangement of the coupling hole and the Stark electrode, the undesirable effect due to the presence of such Stark electrode in the cavity, which affects the Q value and the resonance frequency of the cavity resonator, is eliminated.

Figure 1:
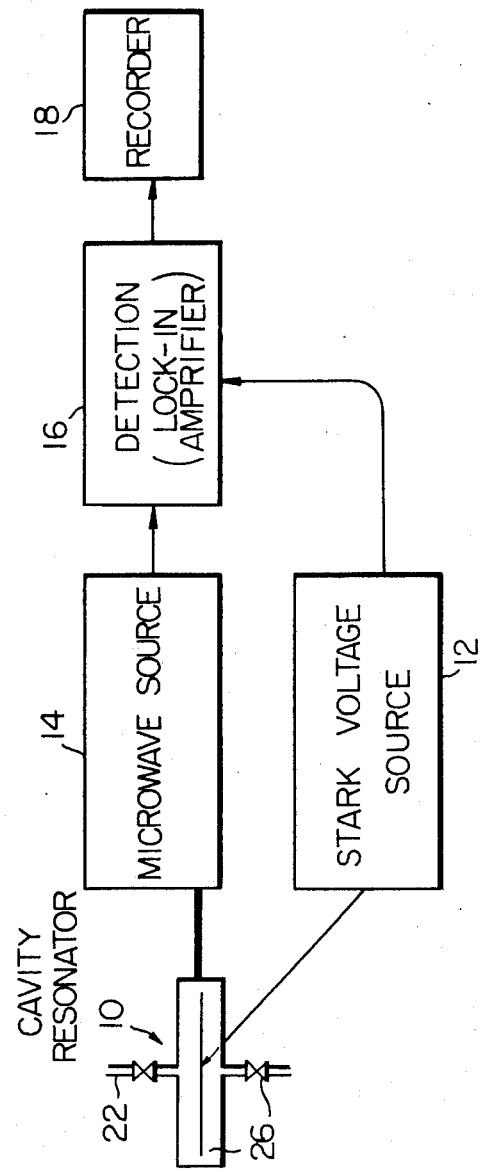
FIG. 1 is a schematic block diagram of an embodiment of a gas analyser constructed in accordance with the present invention.

FIG. 1 is a block diagram of an analyser constructed in accordance with the present invention for performing the present method. The gas analyser shown in this figure comprises a cavity resonator 10 having a rectangular cross section, a microwave source 14, a detection system 16 including a detector and a lock-in type amplifier and a recorder 18. Although the cross section of the cavity is shown as rectangular in this embodiment, it should be recognized that any other configuration such as circular etc. can also be used in the present invention without any degradation of the performance of the analyser. A metal plate is disposed in the center portion of the cavity resonator 10 in parallel with the longer side of the rectangular thereof and used as the Stark electrode. After the cavity resonator 10 is filled with a sample gas, an alternative current Stark voltage is applied to the Stark electrode together with a direct current Stark voltage. Since when the direct current Stark voltage is swept the microwave energy applied from the microwave source 14 through the coupling hole to the interior of the cavity 10 is absorbed at a specific value of the direct current Stark voltage which is inherent to the gas molecule in question, the absorption is picked-up by the lock-in amplifier 16 to record it by the recorder 18 as an absorption spectrum. Thus, the spectrum of the sample gas can be obtained.

FIG. 2 is a cross sectional side view of an embodiment of the cavity resonator 10 shown in FIG. 1 and FIG. 3 is a plane view of the same in partially cross section. As mentioned previously, the resonator is rectangular one operating in $TE_{10n}$ mode and has a cavity region 21 within which the sample gas is introduced. One end of the cavity 21 is closed by a wall having a coupling hole 24, the opposite end of which is closed by a floating contact piston member 25. On the right and left inner walls of the cavity 21, dielectric spacers 27 of such as Teflon (trademark of DuPont) are provided respectively. Also within the cavity 21, a metal plate 26 is provided at the center of the shorter side of the rectangular cavity 21 and in parallel with the longer side thereof and extends throughout the length of the cavity. The metal plate 26 which is used as the Stark electrode is vertically of a microwave electric field produced within the cavity by the microwave supplied from the microwave source 14 through the coupling hole. The cavity is further provided with a sample gas inlet 22 and a gas exit 23 as mentioned previously. The position of the floating contact piston member 25 within the cavity may be regulatable externally by means of a suitable regulation means 30. The Stark electrode 26 is suitably connected through a connector 28 to the Stark power supply 12.

In the present analyser, it is possible to observe simultaneously a plurality of molecular spectra by sweeping the direct current Stark electric field within a range from 0 KV/cm to several tens KV/cm and to identify the molecules from the values of the respective absorption spectra and the spectral patterns thereof. Particularly, in a case where a specific molecule is to be observed, the resonance frequency of the resonator may be set at or around an absorption frequency of the molecule under no electric field. By this setting, such high Stark field voltage as several tens KV/cm will become unnecessary. Therefore, it is preferable to make the resonance frequency of the cavity resonator of the present invention analyser tunable within a certain range. This is easily achieved by providing the floating contact piston member 25 which is shiftable in the longitudinal direction of the cavity at one end of the cavity opposite to the end thereof having the coupling hole 24.

Figure 4:
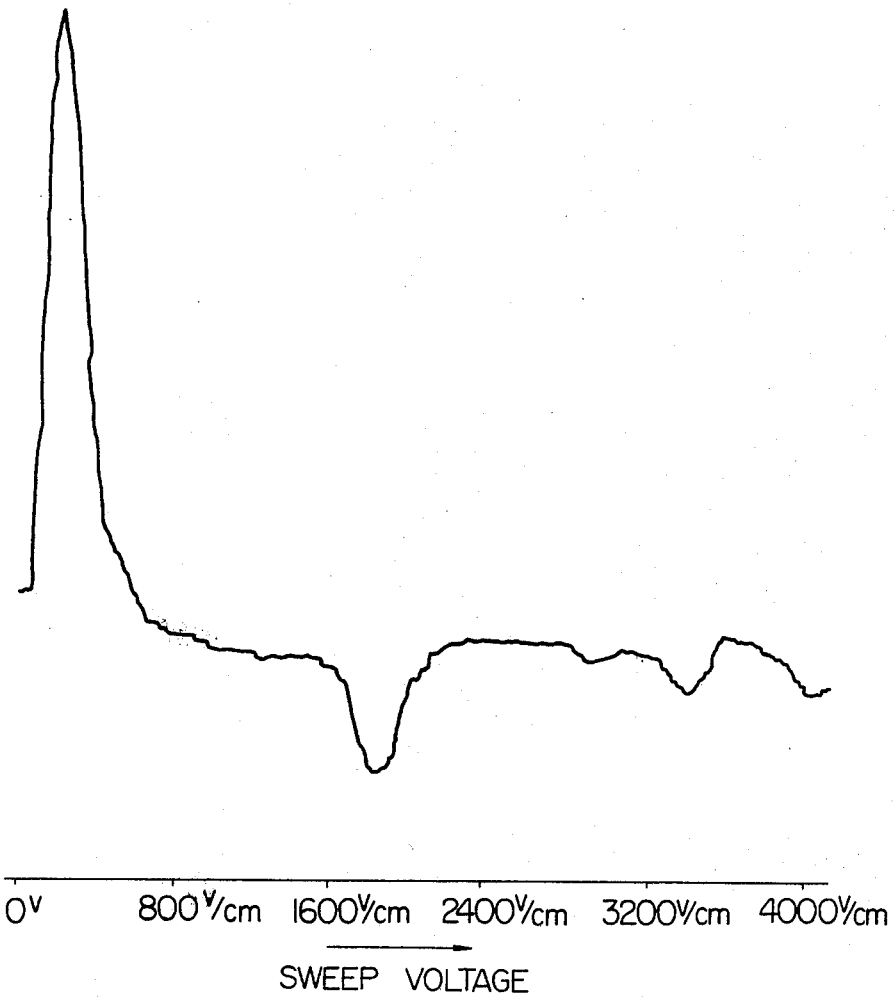
FIGS. 4 to 9 are examples of experimental results obtained by the present invention.
Figure 5:
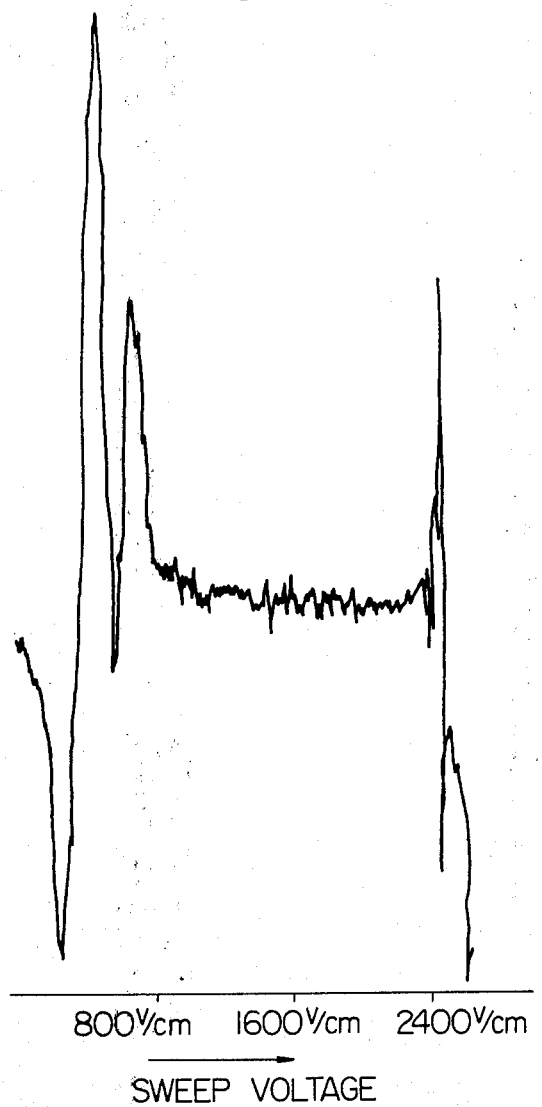
Figure 6:
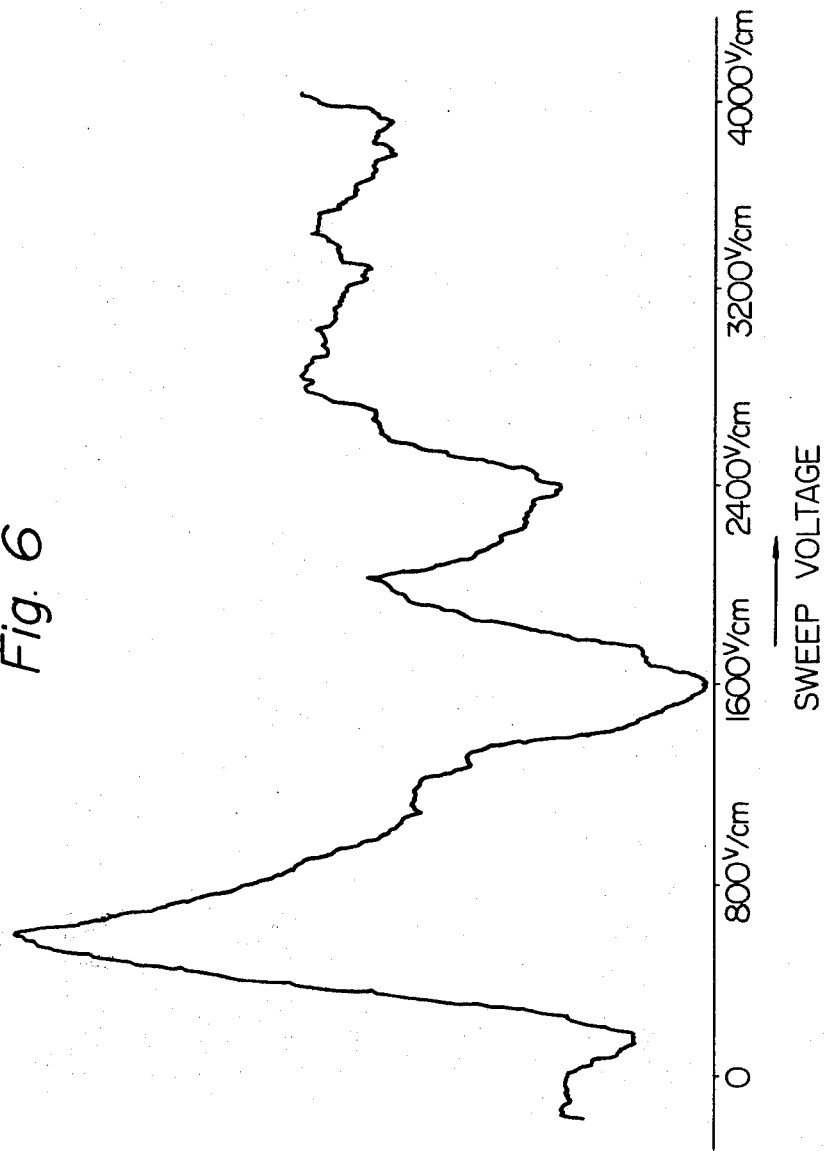

FIGS. 4, 5 and 6 show spectra obtained by sweeping the D.C. Stark voltage for various resonance frequencies.

FIG. 4 is the Stark sweeping spectrum of acrolein obtained by the present apparatus shown in FIG. 1 under the conditions of fixed 8902.50 $MH_z$ resonance frequency and 0.11 Torr cavity inner pressure.

FIG. 5 is the spectrum of methylisocyanate where the resonance frequency is fixed at 8740.5 $MH_z$.

FIG. 6 is that of ammonia where the resonance frequency is 8826 $MH_z$ and the inner pressure is 0.102 Torr.

Figures 7, 8:
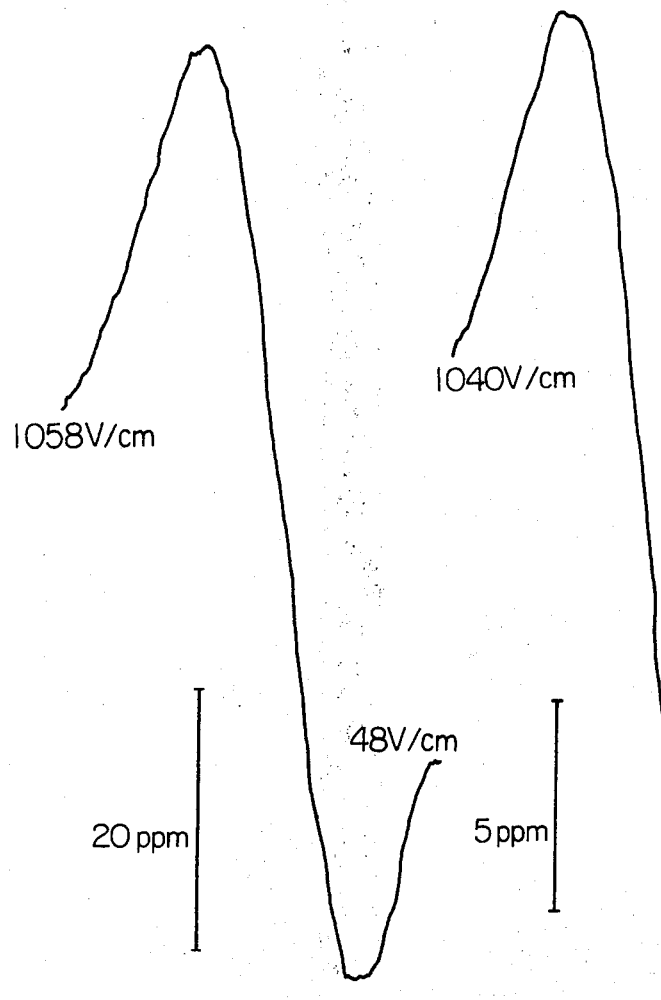

FIGS. 7 and 8 show further examples of the Stark sweeping spectra which demonstrate the remarkably high sensitivity of this spectrometer. FIG. 7 is that of formaldehyde in a standard air sample including 72 ppm formaldehyde with the resonance frequency being 8886.9 $MH_z$ and FIG. 8 is that of formaldehyde directly obtained by using an automobile exhaust gas as a sample gas, the magnitude of this spectrum corresponding to 24 ppm. The signal-noise ratio in FIGS. 7 and 8 has led to the minimum detectable absorption coefficient of $6.0 \times 10^{-13}$ $cm^{-1}$.

Figure 9:

FIG. 9 is another spectrum of formaldehyde of 0.5 ppm.

As described hereinbefore, since the present invention is a spectrometer using microwave energy, the identification of molecules is precise. In addition to this advantage, since the present analyser utilizes the cavity resonator, it is very compact and the sensitivity thereof is very high. Furthermore, since the sweeping is to simply vary the D.C. Stark voltage, the construction of the analyser itself is very simple. Other advantages than those mentioned as above will be obviously appreciated by those skilled in the art.

What is claimed is:

1. A gas analysing method comprising the steps of introducing a gas sample into a microwave rectangular cavity resonator having a Stark electrode;
causing the resonator to resonate at a fixed microwave frequency;
applying an alternating current Stark voltage as well as a direct current Stark voltage to the Stark electrode;
varying the magnitude of the direct current Stark voltage; and
observing the absorption spectrum of the gas sample.

2. A gas analysing method as set forth in claim 1 wherein the resonance frequency of the cavity is varied for analysis of different molecules.

3. A gas analyser comprising
a microwave rectangular cavity resonator having a Stark electrode disposed therein,
means for applying an alternating current Stark voltage and a direct current Stark voltage to the Stark electrode and for varying the magnitude of the direct current Stark voltage,
means for supplying microwave energy of fixed frequency to the rectangular cavity,
a phase sensitive detector connected to the Stark voltage applying means and to the microwave unit, and
a recorder connected to the phase-sensitive detector.

4. A gas analyser as set forth in claim 3 wherein the rectangular cavity of the cavity resonator comprises an end wall provided with a coupling hole through which microwave energy is supplied to the rectangular cavity and a floating contact member disposed to directly face the end wall with the end wall and the floating contact member being disposed at opposite ends of the Stark electrode.

5. A gas analyser as set forth in claim 4 wherein the resonator includes means for varying the resonance frequency thereof.

* * * * *